(12) United States Patent
Bliss et al.

(10) Patent No.: US 8,597,343 B2
(45) Date of Patent: Dec. 3, 2013

(54) STENT WITH CONSTANT STIFFNESS ALONG THE LENGTH OF THE STENT

(75) Inventors: Richard Bliss, Cloverdale, CA (US); Justin Goshgarian, Santa Rosa, CA (US); Rui Lam, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 191 days.

(21) Appl. No.: 12/693,586

(22) Filed: Jan. 26, 2010

(65) Prior Publication Data
US 2011/0071619 A1 Mar. 24, 2011

Related U.S. Application Data

(60) Provisional application No. 61/243,581, filed on Sep. 18, 2009, provisional application No. 61/243,578, filed on Sep. 18, 2009, provisional application No. 61/243,582, filed on Sep. 18, 2009, provisional application No. 61/243,592, filed on Sep. 18, 2009, provisional application No. 61/243,597, filed on Sep. 18, 2009, provisional application No. 61/243,600, filed on Sep. 18, 2009.

(51) Int. Cl.
*A61F 2/06* (2013.01)
(52) U.S. Cl.
USPC .......................................... 623/1.16; 623/1.22
(58) Field of Classification Search
USPC ...................... 623/1.12, 1.16, 1.22
See application file for complete search history.

(56) References Cited

U.S. PATENT DOCUMENTS

| | | | |
|---|---|---|---|
| 2,153,936 A | 4/1939 | Owens et al. |
| 3,185,185 A | 5/1965 | Pfund |
| 4,047,544 A | 9/1977 | Seaborn et al. |
| 4,886,062 A | 12/1989 | Wiktor |
| 5,019,090 A | 5/1991 | Pinchuk |
| 5,092,877 A | 3/1992 | Pinchuk |
| 5,133,732 A | 7/1992 | Wiktor |
| 5,226,913 A | 7/1993 | Pinchuk |
| 5,304,200 A | 4/1994 | Spaulding |
| 5,314,472 A | 5/1994 | Fontaine |
| 5,324,472 A | 6/1994 | Page et al. |
| 5,370,683 A | 12/1994 | Fontaine |
| 5,443,498 A | 8/1995 | Fontaine |

(Continued)

FOREIGN PATENT DOCUMENTS

| | | |
|---|---|---|
| EP | 0 565 251 A1 | 10/1993 |
| EP | 945107 | 9/1999 |

(Continued)

*Primary Examiner* — Thomas J Sweet
*Assistant Examiner* — Seema Mathew

(57) ABSTRACT

A stent includes a wave form that includes a plurality of struts and a plurality of crowns. Each crown connects two adjacent struts within the wave form. The wave form is wrapped around a longitudinal axis at a pitch angle to define a plurality of turns and has a central portion and two end portions located on opposite sides of the central portion. At least some of the struts located in the end portions have lengths longer than an average length of all of the struts of the wave form. The stent also includes a plurality of connections. Each connection connects selected crowns from adjacent turns. The connections are positioned along the stent substantially equally so that a density of the number of connections of the end portions is substantially equal to a density of the number of connections of the central portion.

5 Claims, 5 Drawing Sheets

(56) References Cited

U.S. PATENT DOCUMENTS

| | | | |
|---|---|---|---|
| 5,527,354 A | 6/1996 | Fontaine et al. | |
| 5,549,663 A | 8/1996 | Cottone, Jr. | |
| 5,575,818 A * | 11/1996 | Pinchuk | 623/1.15 |
| 5,653,727 A | 8/1997 | Wiktor | |
| 5,716,396 A | 2/1998 | Williams, Jr. | |
| 5,749,919 A * | 5/1998 | Blanc | 623/1.22 |
| 5,800,456 A | 9/1998 | Maeda et al. | |
| 5,895,406 A | 4/1999 | Gray et al. | |
| 5,902,266 A | 5/1999 | Leone et al. | |
| 5,913,897 A * | 6/1999 | Corso et al. | 623/1.15 |
| 5,968,091 A * | 10/1999 | Pinchuk et al. | 623/1.16 |
| 6,042,597 A * | 3/2000 | Kveen et al. | 623/1.15 |
| 6,117,165 A | 9/2000 | Becker | |
| 6,136,023 A | 10/2000 | Boyle | |
| 6,190,406 B1 | 2/2001 | Duerig et al. | |
| 6,203,569 B1 | 3/2001 | Wijay | |
| 6,287,333 B1 * | 9/2001 | Appling et al. | 623/1.22 |
| 6,342,067 B1 | 1/2002 | Mathis et al. | |
| 6,355,059 B1 * | 3/2002 | Richter et al. | 623/1.17 |
| 6,423,084 B1 * | 7/2002 | St. Germain | 606/198 |
| 6,423,091 B1 | 7/2002 | Hojeibane | |
| 6,432,132 B1 | 8/2002 | Cottone et al. | |
| 6,447,540 B1 | 9/2002 | Fontaine et al. | |
| 6,503,270 B1 | 1/2003 | Richter et al. | |
| 6,610,086 B1 * | 8/2003 | Kock et al. | 623/1.22 |
| 6,656,219 B1 | 12/2003 | Wiktor | |
| 6,730,117 B1 | 5/2004 | Tseng et al. | |
| 6,736,844 B1 | 5/2004 | Glatt et al. | |
| 6,878,162 B2 | 4/2005 | Bales et al. | |
| 6,923,828 B1 | 8/2005 | Wiktor | |
| 6,969,402 B2 | 11/2005 | Bales et al. | |
| 7,004,968 B2 | 2/2006 | Lootz et al. | |
| 7,018,403 B1 * | 3/2006 | Pienknagura | 623/1.15 |
| 7,108,714 B1 * | 9/2006 | Becker | 623/1.15 |
| 7,112,216 B2 * | 9/2006 | Gregorich | 623/1.15 |
| 7,169,175 B2 | 1/2007 | Cottone, Jr. et al. | |
| 7,329,277 B2 * | 2/2008 | Addonizio et al. | 623/1.22 |
| 7,657,939 B2 * | 2/2010 | Strauss et al. | 726/23 |
| 7,803,180 B2 * | 9/2010 | Burpee et al. | 623/1.15 |
| 7,862,607 B2 * | 1/2011 | McDermott et al. | 623/1.16 |
| 7,942,922 B2 * | 5/2011 | Addonizio et al. | 623/1.15 |
| 8,052,738 B2 * | 11/2011 | Craven | 623/1.16 |
| 8,226,705 B2 * | 7/2012 | Griswold | 623/1.22 |
| 8,333,799 B2 * | 12/2012 | Bales et al. | 623/1.22 |
| 8,366,765 B2 * | 2/2013 | Baldwin et al. | 623/1.22 |
| 8,372,135 B2 * | 2/2013 | Addonizio et al. | 623/1.15 |
| 8,500,793 B2 * | 8/2013 | Zipse et al. | 623/1.22 |
| 8,500,794 B2 * | 8/2013 | Beach et al. | 623/1.22 |
| 2002/0095208 A1 | 7/2002 | Gregorich et al. | |
| 2002/0111669 A1 * | 8/2002 | Pazienza et al. | 623/1.15 |
| 2003/0069633 A1 * | 4/2003 | Richter et al. | 623/1.22 |
| 2003/0083736 A1 | 5/2003 | Brown et al. | |
| 2003/0167084 A1 * | 9/2003 | Orlowski | 623/1.15 |
| 2004/0034402 A1 * | 2/2004 | Bales et al. | 623/1.2 |
| 2004/0044401 A1 * | 3/2004 | Bales et al. | 623/1.22 |
| 2004/0054398 A1 * | 3/2004 | Cully et al. | 623/1.15 |
| 2004/0143318 A1 | 7/2004 | Tseng et al. | |
| 2004/0199243 A1 * | 10/2004 | Yodfat | 623/1.16 |
| 2006/0030934 A1 * | 2/2006 | Hogendijk et al. | 623/1.22 |
| 2006/0079955 A1 * | 4/2006 | Brown | 623/1.22 |
| 2007/0005126 A1 * | 1/2007 | Tischler | 623/1.15 |
| 2007/0129786 A1 * | 6/2007 | Beach et al. | 623/1.15 |
| 2007/0250148 A1 * | 10/2007 | Perry et al. | 623/1.11 |
| 2008/0097580 A1 | 4/2008 | Dave | |
| 2008/0097582 A1 * | 4/2008 | Shanley et al. | 623/1.22 |
| 2008/0183273 A1 | 7/2008 | Mesana et al. | |
| 2008/0288053 A1 | 11/2008 | Addonizio et al. | |
| 2008/0289389 A1 | 11/2008 | Fitch et al. | |
| 2008/0294241 A1 | 11/2008 | Addonizio et al. | |
| 2008/0306583 A1 | 12/2008 | Bashiri et al. | |
| 2008/0319529 A1 * | 12/2008 | Krivoruchko et al. | 623/1.16 |
| 2008/0319534 A1 | 12/2008 | Birdsall et al. | |
| 2008/0319535 A1 * | 12/2008 | Craven et al. | 623/1.22 |
| 2009/0005848 A1 | 1/2009 | Strauss et al. | |
| 2009/0024207 A1 | 1/2009 | Addonizio et al. | |
| 2009/0036976 A1 * | 2/2009 | Beach et al. | 623/1.22 |
| 2009/0259294 A1 * | 10/2009 | Cully et al. | 623/1.22 |
| 2009/0306766 A1 * | 12/2009 | McDermott et al. | 623/1.16 |
| 2010/0004725 A1 * | 1/2010 | Zipse et al. | 623/1.2 |
| 2011/0071615 A1 * | 3/2011 | Griswold | 623/1.15 |
| 2011/0230957 A1 * | 9/2011 | Bonsignore et al. | 623/1.16 |
| 2012/0078344 A1 * | 3/2012 | Kao | 623/1.16 |
| 2012/0303112 A1 * | 11/2012 | Armstrong et al. | 623/1.16 |
| 2013/0274864 * | 10/2013 | Bienvenu et al. | 623/1.16 |

FOREIGN PATENT DOCUMENTS

| | | |
|---|---|---|
| EP | 1155664 | 11/2007 |
| GB | 2281865 | 3/1995 |
| WO | WO 01/89421 A2 | 11/2001 |
| WO | WO2007/095466 | 8/2007 |
| WO | WO2008/028964 | 3/2008 |
| WO | WO2008/100783 | 8/2008 |

* cited by examiner

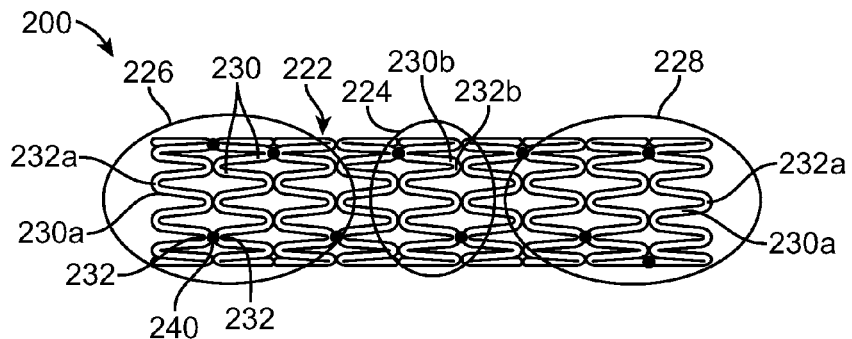
FIG. 6
FIG. 7 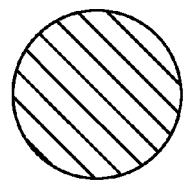 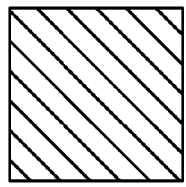 
(a)   (b)   (c)
FIG. 8 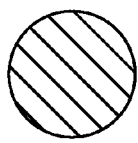 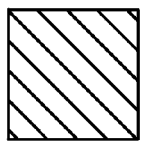 
(a)   (b)   (c)
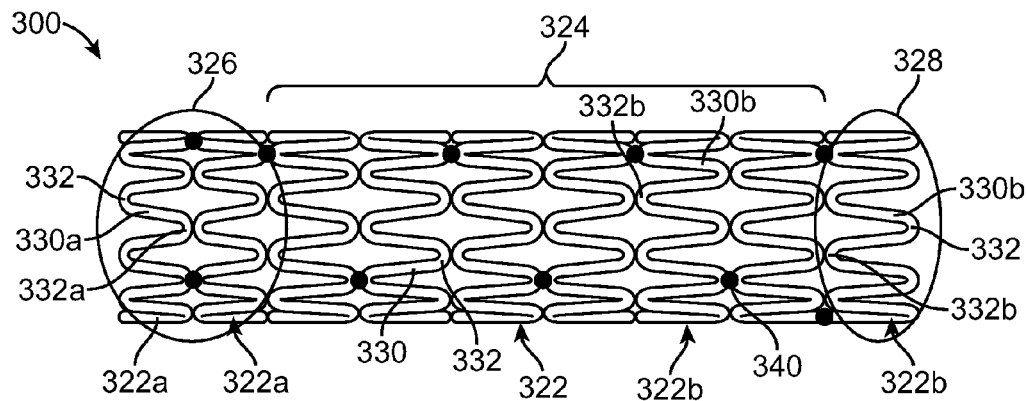
FIG. 9

STENT WITH CONSTANT STIFFNESS ALONG THE LENGTH OF THE STENT

CROSS-REFERENCE TO RELATED APPLICATIONS

This application claims the benefit of priority from U.S. Provisional Patent Application Ser. No. 61/243,581, filed on Sep. 18, 2009, the entire content of which is incorporated herein by reference. This application also claims the benefit of priority from U.S. Provisional Patent Application Ser. No. 61/243,578, 61/243,582, 61/243,592, 61/243,597, and 61/243,600, all filed on Sep. 18, 2009, the entire contents of all of which are incorporated herein by reference.

BACKGROUND OF THE INVENTION

1. Field of the Invention

The present invention is generally related to a stent having a constant stiffness along the length of the stent, and a method for manufacturing a stent having a constant stiffness along the length of the stent.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a delivery system that includes a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle.

When tracking stents on a delivery system in the lumen to a deployment site, if the stiffness of the stent varies along the length of the stent, an increase in end flaring and/or strut/crown lifting may occur. Specifically, when there is a transition from a lower stiffness to a higher stiffness, or vice versa, a "kink" point may occur at the transition. The result of the "kink" point is that the parts of the surrounding structure of the stent may interfere with each other and cause lifting. This may also occur at the end of the stent with the transition of the delivery system, which has a low stiffness, to the stent, which has a high stiffness.

SUMMARY OF THE INVENTION

It is an aspect of the present invention to provide a stent that has substantially constant stiffness along the length of the stent to reduce the likelihood of developing a "kink" point during delivery of the stent to the target deployment site.

In an embodiment or the present invention, a stent includes a wave form that includes a plurality of struts and a plurality of crowns. Each crown connects two adjacent struts within the wave form. The wave form is wrapped around a longitudinal axis at a pitch angle to define a plurality of turns and has a central portion and two end portions located on opposite sides of the central portion. At least some of the struts located in the end portions have lengths longer than an average length of all of the struts of the wave form. The stent also includes a plurality of connections. Each connection connects selected crowns from adjacent turns. The connections are positioned along the stent substantially equally so that a density of the number of connections of the end portions is substantially equal to a density of the number of connections of the central portion.

In an embodiment of the invention, there is provided a method of manufacturing a stent. The method includes forming a wave form having a plurality of struts and a plurality of crowns. Each crown connects two adjacent struts. The wave form has a central portion and two end portions located on opposite sides the central portion. At least some of the struts located in the end portions are formed to have lengths longer than an average length of all of the struts of the wave form. The method also includes wrapping the wave form about a longitudinal axis at a pitch angle to form a helical coil having a plurality of turns, and connecting selected crowns of adjacent turns with connections so that the connections are positioned along the stent substantially equally so that a density of the number of connections of the end portions is substantially equal to a density of the number of connections of the central portion.

In an embodiment of the invention, a stent includes a wave form that include a plurality of struts and a plurality of crowns. Each crown connects two adjacent struts within the wave form. The wave form is wrapped around a longitudinal axis to define a plurality of turns. The wave form has a central portion and two end portions located on opposite sides of the central portion. The turns of the central portion have a substantially constant pitch angle of less that 90° relative to the longitudinal axis, and the turns of the end portions transition from the substantially constant pitch angle of the central portion to an angle of about 90° relative to the longitudinal axis. The stent also includes a plurality of connections. Each connection connects selected crowns from adjacent turns. The connections are positioned along the stent substantially equally so that a density of the number of connections of the end portions is substantially equal to a density of the number of connections of the central portion.

In an embodiment of the invention, there is provided a method of manufacturing a stent. The method includes forming a wave form having a plurality of struts and a plurality of crowns. Each crown connects two adjacent struts. The wave form has a central portion and two end portions located on opposite sides the central portion. The method also includes wrapping the wave form about a longitudinal axis to define a plurality of turns so that a first turn of a first end portion defines a first angle of about 90° relative to the longitudinal axis, a second turn of the first end portion defines a second angle of less than 90°, and the turns of the central portion define a third angle of less than the second angle. The method also includes connecting selected crowns of adjacent turns with connections so that the connections are positioned along the stent substantially equally so that a density of the number of connections of the end portions is substantially equal to a density of the number of connections of the central portion.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 6 schematically depicts a stent according to an embodiment of the present invention;

FIGS. 7a-7c depict cross sections of crowns and/or struts of a stent according to embodiments of the present invention;

FIGS. 8a-8c depict cross sections of crowns and/or struts of a stent having decreased stiffness as compared to the crowns and struts of FIGS. 7a-7c, respectively, according to embodiments of the present invention;

FIG. 9 schematically depicts a stent according to an embodiment of the present invention;

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
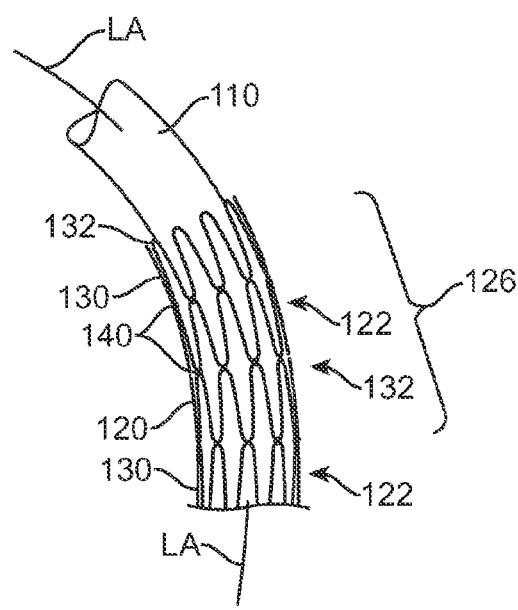
FIG. 1 schematically depicts an end of a stent on a delivery system as the stent is tracked to a target deployment site in a lumen.

FIG. 1 schematically illustrates a portion of a stent 100 that is crimped onto a delivery system 110 and is being tracked to a target deployment site. Only one end portion 126 of the stent 100 is illustrated in FIG. 1. As illustrated, the stent 100 includes a wave form 120 that includes a plurality of struts 130 and a plurality of crowns 132. Each crown 132 connects two adjacent struts 130. The wave form 120 is wrapped around a longitudinal axis LA of the stent 100, to define a plurality of turns 122, The longitudinal axis LA of the stent 100 is illustrated in FIG. 1 as being curved, due to the bending of the delivery system 110 and the stent 100 as it is being tracked through a curved lumen to the target deployment site.

As illustrated in FIG. 1, selected crowns 132 of adjacent turns 122 of the wave form 120 are connected to each other with connections 140. The connections 140 provide local areas of stiffness, which may assist in controlling the expansion of the stent 100 when the stent 100 is expanded at the target deployment site. As discussed above, it has been found that when the stiffness along the length of the stent 100 is not constant, the transitions from lower stiffness to higher stiffness, or vice versa, may become problematic, because a "kink" point may occur at the transition. A "kink" point may result in the surrounding crowns 132 and struts 130 interfering with each other, which may cause lifting of a crown 132a outwardly and away from the delivery system 110, as depicted in FIG. 1.

Figure 2:
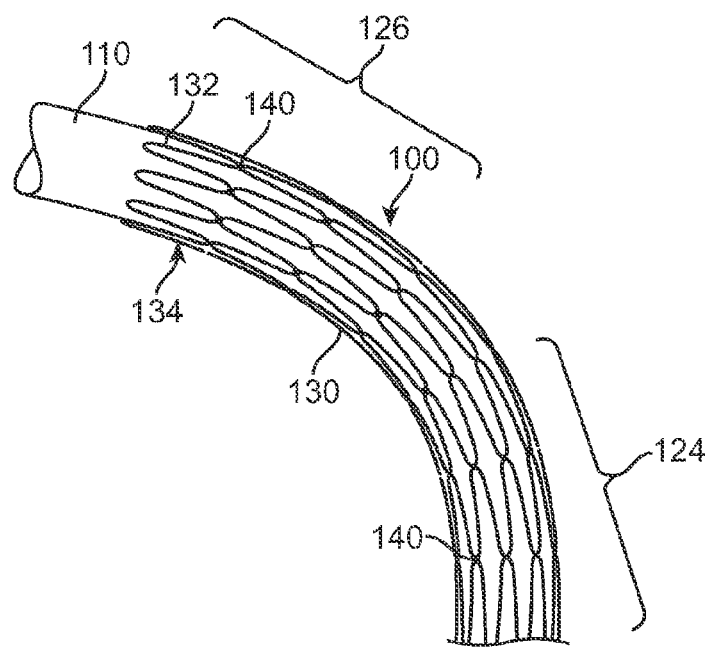
FIG. 2 schematically depicts the stent of FIG. 1 as it is further tracked to the target deployment site.

In the embodiment illustrated in FIG. 1, the connections 140 in the end portion 126 have a density, i.e. the number of crowns 132 per turn 122 being connected, that is relatively high as compared to the density of connections 140 of a central portion 124 of the stent 100, a portion of which is illustrated in FIG. 2.

FIG. 2 illustrates what may happen when the stent 100 is tracked around a curve and the stiffness of the end portion 126 of the stent 100 is much greater than the stiffness of the underlying delivery system 110. As illustrated an end crown 134 of the end portion 126 has flared outward and away from the delivery system 110, which is undesirable.

Figure 3:
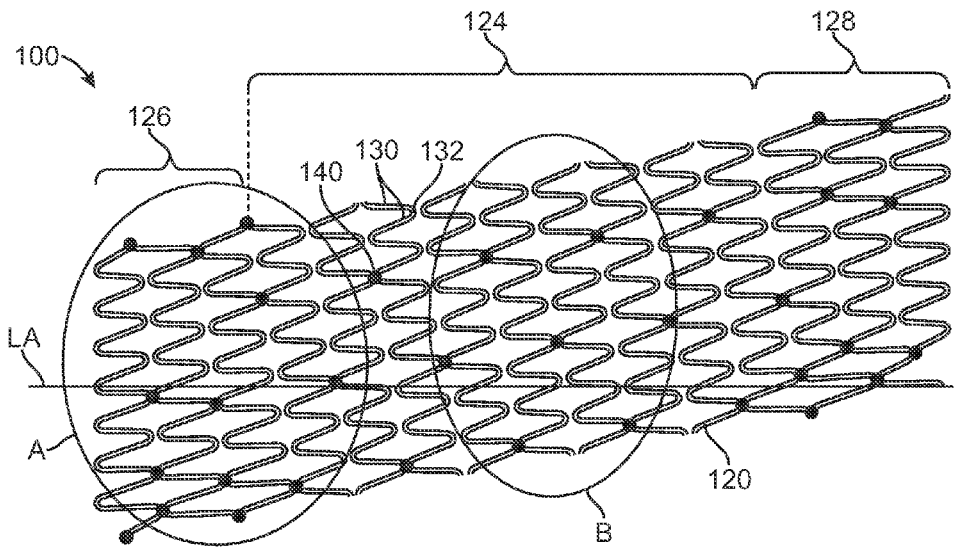
FIG. 3 schematically depicts the stent of FIGS. 1 and 2 in an "unrolled" configuration.

FIG. 3 illustrates the stent 100 of FIGS. 1 and 2 in an "unrolled" state, i.e., the stent 100 has been slit along a straight line that is parallel to the longitudinal axis LA of the stent 110 and unrolled to a substantially flat configuration, so that the density of the connections 140 may be more easily depicted. As illustrated in FIG. 3, the end portion 126 has a higher density of connections 140 than the central portion 124 (i.e. when generally comparing the circled area A versus the circled area B in FIG. 3). As discussed above, the higher density of connections 140 in the end portion 126 may cause the stiffness of the end portion 126 to be greater than the stiffness of the central portion 124, which may cause unconnected crowns to flare outwardly during tracking to the target deployment site, as illustrated in FIGS. 1 and 2. It is desirable to minimize or even eliminate such instances of flaring so that the stent may be tracked to the target deployment site more easily.

Figure 4:
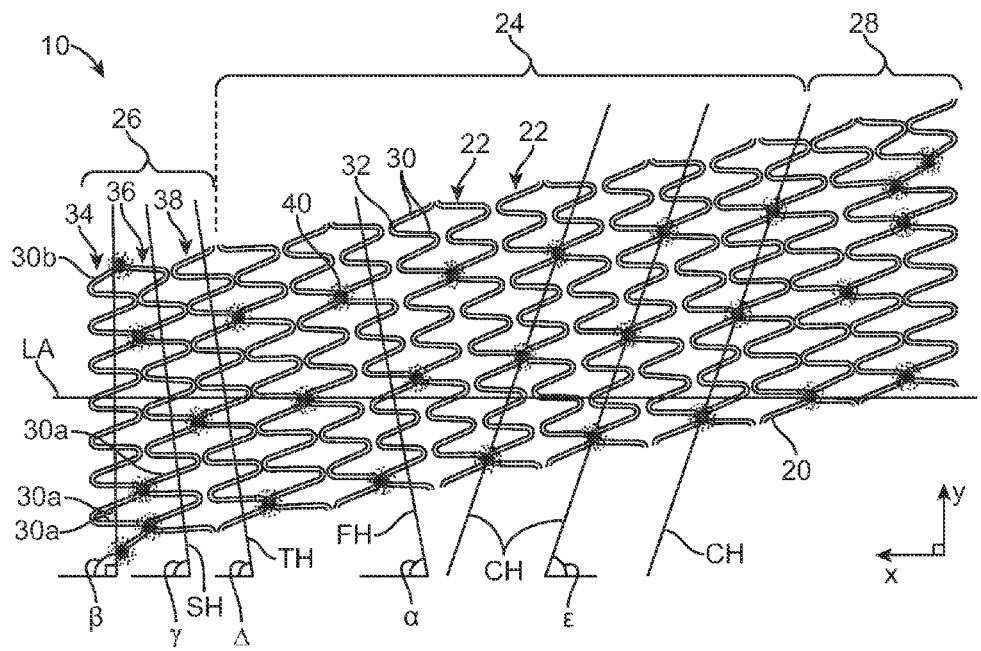
FIG. 4 schematically depicts a stent according to an embodiment of the present invention in an "unrolled" configuration.

FIG. 4 illustrates a stent 10 according to an embodiment of the present invention. The stent 10 is generally cylindrical in shape and has a longitudinal axis LA extending through the center of the stent 10. FIG. 4 illustrates the stent 10 in an "unrolled" state, similar to the stent 110 depicted in FIG. 3. The stent 10 includes a continuous wave form 20 that includes a plurality of turns 22 that are created when the wave form 20 is wrapped around the longitudinal axis LA during manufacturing of the stent 10. The stent 10 generally includes a central portion 24 and two end portions, a first end portion 26 and a second end portion 28, that are located on opposite sides of the central portion 24 and are mirror images of each other.

As illustrated in FIG. 4, the wave form 20 includes a plurality of struts 30 and a plurality of crowns 32. Each crown 32 is a curved portion or turn within the wave form 20 that connects adjacent struts 30 to define the continuous wave form 20. As shown in FIG. 4, the struts 30 are substantially straight portions of the wave form 20. In other embodiments, the struts 30 may be slightly bent or have other shapes, such as a sinusoidal wave, for example.

As illustrated in FIG. 4, the wave form 20 is wrapped around the longitudinal axis LA at different pitches so that the wave form 20 generally defines a helical coil in the central portion 24 having a first helical angle, or first pitch angle $\alpha$, to define a first helix FH, and also defines ends that are substantially square or perpendicular with the longitudinal axis LA. As illustrated, the first end portion 26, include a first turn 34 that is wrapped about the longitudinal axis LA at an angle $\beta$ of about 90° so that the stent 10 has an end that is substantially square or perpendicular to the longitudinal axis LA. As illustrated, the first turn 34 includes struts 30 having different lengths, and at least some of the struts 30 have a length that is longer, labeled 30a in FIG. 4, than the average length of all of the struts 30 of the stent 10. The first turn 34 may also include struts that have a length that is shorter, labeled 30b in FIG. 4, than the average length of all of the struts 30 of the stent 10.

The first end portion 26 also includes a second turn 36 that is a continuation of the wave form 20 from the first turn 34. The second turn 36 is wrapped about the longitudinal axis LA at a second pitch angle $\gamma$ that is less than 90° but greater than the first pitch angle $\alpha$, to define a second helix SH. Additional turns may be part of the first end portion 26, such as a third turn 38, and may be configured to provide a more gradual transition between the first turn 34 that is wrapped about the longitudinal axis LA at about 90° and the first pitch angle α of the central portion 24. In the illustrated embodiment, the third turn 38 is wrapped about the longitudinal axis LA at a third pitch angle Δ, which is greater than the first pitch angle α but less than the second pitch angle γ, to define a third helix TH.

The presence of the longer struts 30a in the first end portion 26 may cause the stent 10 to expand unevenly, as compared to central portion 24, which generally includes struts 30 having a shorter length, when an internal pressure is applied to the stent 10. Therefore, it may be desirable to connect the crown 32 that connects a longer strut 30a within a turn 22 to a crown 32 of the next turn in order to stiffen that area and impede the expansion of the part of the wave form 20 that contains the longer strut 30a.

The number of turns 22 about the longitudinal axis and the first helical angle α may be determined by the particular specifications of the stent 10, such as the desired unexpanded and expanded diameters and the length of the stent, as well as the size (e.g., diameter) and particular material of the wire or strip of material. The illustrated embodiments are not intended to be limiting in any way.

The stent 10 also includes a plurality of connections 40 that are configured to connect selected crowns 32 of adjacent turns 22 so that when the stent is in an unexpanded condition, as generally depicted in FIG. 1, the plurality of connections 40 generally lie along a connection helix CH defined by a connection helical angle ε relative to the longitudinal axis LA. As illustrated in FIG. 4, the connection helix CH is oriented substantially opposite to the first helix FH described above such that the connection helical angle ε is between 0° and 90° when using a coordinate system that is opposite the coordinate system depicted in FIG. 4 (i.e., the positive x axis runs from left to right rather than from right to left).

The connections 40 may be created by fusing the selected crowns 32 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion.

In an embodiment, the connections 40 may be created by welding or soldering the selected crowns 32 together. As used herein, "welding" and "soldering" are defined as heating an additional material that is separate from the selected crowns and applying the heated additional material to the selected crowns 32 so that when the additional material cools, the selected crowns 32 are welded or soldered together.

In an embodiment, the connections 40 may be created by fusing, welding, or soldering an additional piece of material (not shown) that extends between selected crowns 32. The additional piece of material may resemble a strut or a portion of a strut, and may be sized to provide spacing between the selected crowns of two adjacent turns, if desired. The illustrated embodiments are not intended to be limiting in any way.

The connections 40 may be positioned to increase the longitudinal flexibility of the stent 10, when the stent 10 is in an unexpanded, particularly crimped, condition so that the stent 10 may be advanced to the targeted deployment site more easily and without the development of the so-called "kinks" discussed above. The size of the connections 40 may also be varied according to the desired flexibility and rate of expansion for a given area of the stent 10. In general, the larger the connection 40, i.e. the larger the fusion or weld, the greater the stiffness, and the slower the rate of expansion of the stent in the area of the larger connections.

Figure 5:
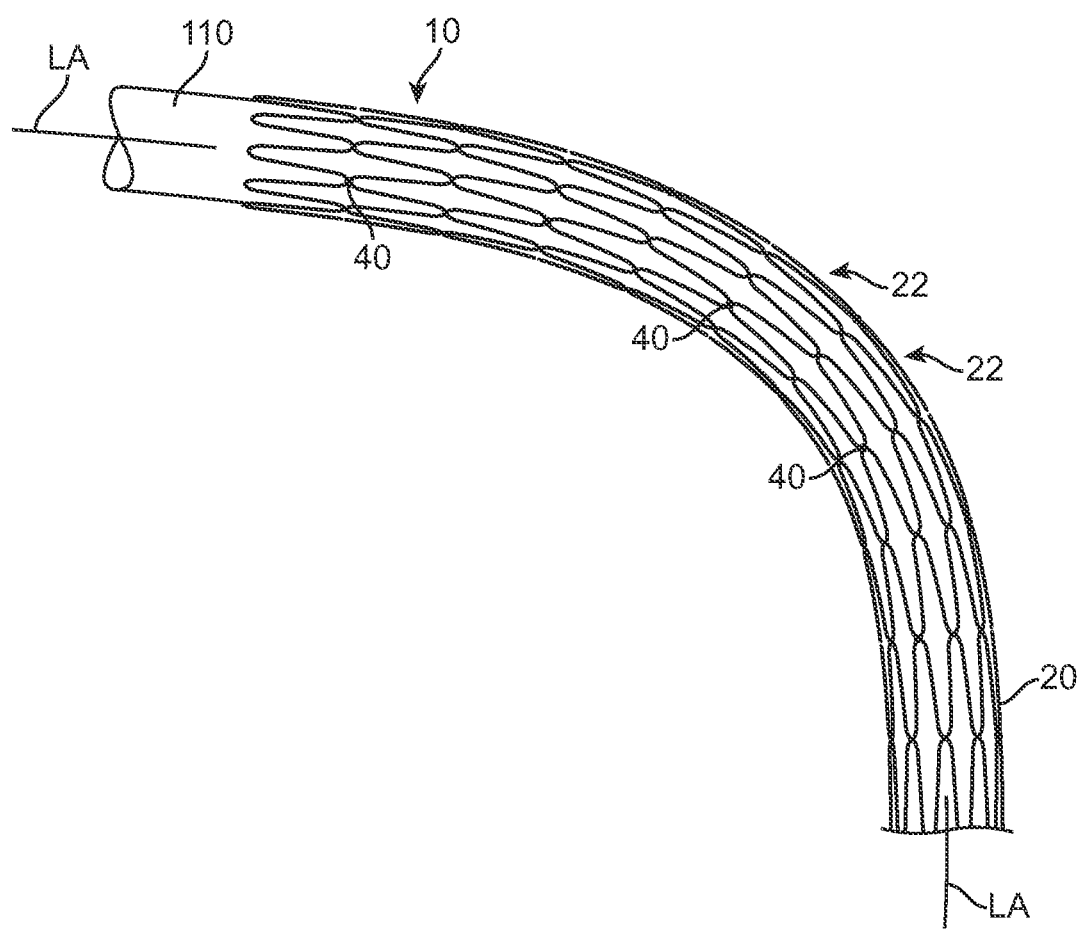
FIG. 5 schematically depicts an end of the stent of FIG. 4 on a delivery system as the stent is tracked to a target deployment site in a lumen.

FIG. 5 illustrates the stent 10 of FIG. 4 on the delivery system 110 while being tracked to the target deployment site in a lumen. As illustrated, the stent 10 has relatively low stiffness along its length, as compared to the stent 100 illustrated in FIGS. 1-3, and therefore may track over a bend with minimal lifting of the crowns 32 and without the development of the so-called "kinks" discussed above. It has been found that when the stiffness is generally consistent across the length of the stent 10, the amount of interference of the crowns 32 and the struts 30 is reduced, and as a result, the amount of lifting or flaring of the crowns 32 is reduced.

It has been found that other stent design attributes, in addition to the density of the connections, have an influence on the stiffness along the length of the stent. For example, the dimensions, i.e., the width and thickness, of the struts and crowns can influence the stiffness of the stent. In an embodiment of a stent that has struts at or near the end of the stent with dimensions (width and thickness) that are larger than the dimensions of the struts in the middle of the stent, the end result is a stent having a higher stiffness at the ends when compared to the middle of the stent.

Such an embodiment is illustrated in FIG. 6, which illustrates a stent 200 having a central portion 224, a first end portion 226 connected to one side of the central portion 224, and a second end portion 228 connected to an opposite side of the central portion 224. The stent 220 has a plurality of turns 222 that are connected with connections 240, like the connections 40 discussed above, at selected crowns 232. The crowns 232 connect adjacent struts 230 within a turn 222. The end portions 226, 228 have crowns 232a and struts 230a that have larger cross-sectional areas, as compared to the crowns 232b and struts 230b of the central portion 224, which may in turn provide the stent 220 with stiffer ends portions 226, 228 and a more flexible central portion 224.

FIGS. 7a-c schematically illustrate embodiments of cross-sections of the crowns 232a and the struts 230a of the end portions 226, 228, while FIGS. 8a-c schematically illustrate embodiments of cross-sections of the crowns 232b and the struts 230b of the central portion 224. For example, the crowns 232a and the struts 230a of the end portions 226, 228 may each have a cross-section that is illustrated in FIG. 7a, while the crowns 232b and the struts 230b may each have a cross-section that is illustrated in FIG. 8a and is shown to be smaller than the cross-section illustrated in FIG. 7a.

The cross-sectional shape of the struts 230 and crowns 232 can also influence the stiffness of the stent 200. For example if the central portion 224 of the stent 200 has a circular cross-section for the struts 230b and crowns 232b, such as the cross-section of FIG. 7a or FIG. 8a, and the end portions 226, 228 have a flattened rectangular cross-section for the struts 230a and crowns 232a, such as the cross-section of FIG. 7c or FIG. 8c, then the end result would be a stent having end portions 226, 228 with a stiffness that is greater than the stiffness of the central portion 224.

FIG. 9 illustrates an embodiment of a stent 300 that includes a plurality of turns 322 that are defined by a plurality of crowns 332 that connect adjacent struts 330. Adjacent turns are connected at selected crowns 332 with connections 340, like the connections 40 discussed above. It has been found that the length of the turn 322 and/or the length of the strut 330 can also influence the stiffness along the length of the stent 300. For example, a long strut length will decrease the number of flexing points between turns 322 along the length of that portion of the stent 300, which will reduce the stiffness along the length of that portion of the stent 300.

For example, as illustrated in FIG. 9, one end portion 326 of the stent 300 includes two turns 322a that are shorter or narrower than the turns 322b of a central portion 324 and the end portion 328. The turns 322a of the end portion 326 include struts 330a that are shorter than the struts 330b of the turns 322b of the central portion 324 and the other end portion 328. Because there are more flexing points, i.e., unconnected crowns 332a in the area of the end portion 326, per length of stent 300, as compared to the unconnected crowns 332b per length of stent 300 in the central portion 324 and the end portion 328, the end portion 326 will be less stiff, or more flexible, than the central portion 324 or the end portion 328.

Figure 10:
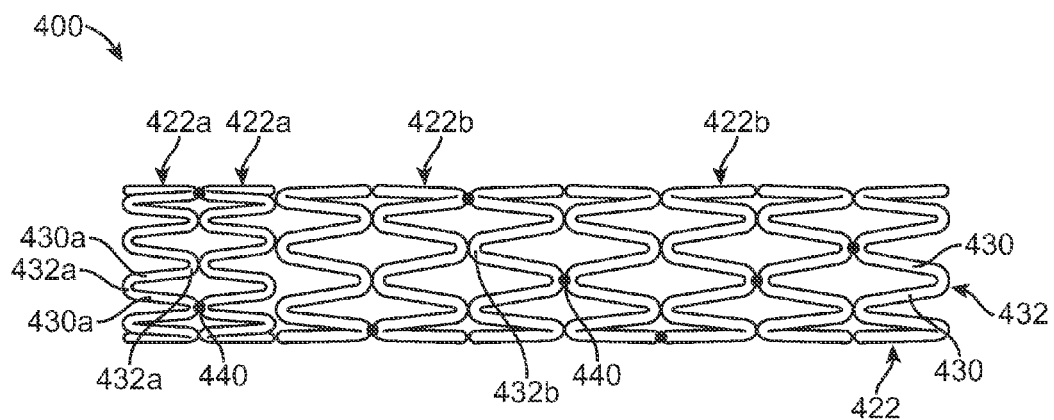
FIG. 10 schematically depicts a stent according to an embodiment of the present invention.

FIG. 10 illustrates an embodiment of a stent 400 that includes a plurality of turns 422 that include a plurality of crowns 432 that connect adjacent struts 430 within a turn 422. Selected crowns 432 of adjacent turns 422 may be connected with connections 440, like the connections 40 discussed above. In the illustrated embodiment, the stent 400 includes two turns 422a that each have a greater number of crowns 432a as compared to the rest of the turns 422b of the stent 400. It has been found that a greater number of crowns 432a may increase the stiffness of the stent 400 in the area of the greater number of crowns 432a, because the greater number of crowns 432a may reduce an amount of room the struts 430a and attached crowns 430a have to move while the stent 400 is being bent as it is tracked to the deployment site.

Figure 11:
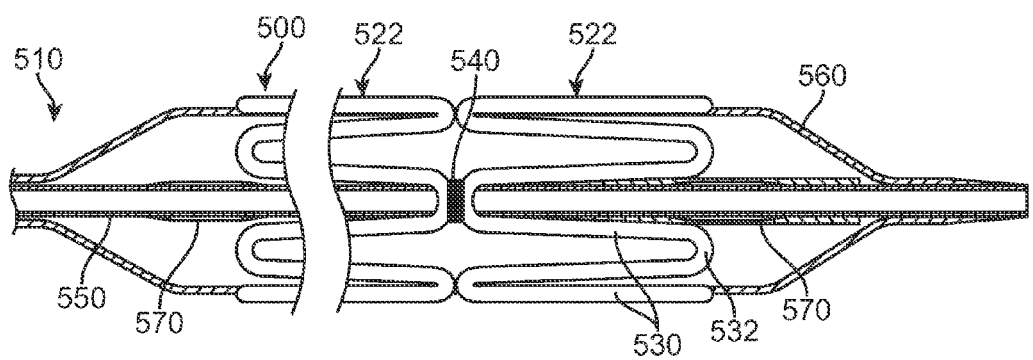
FIG. 11 schematically depicts a delivery system and a stent according to an embodiment of the present invention.

FIG. 11 illustrates an embodiment of a delivery system 510 on which a stent 500 is mounted for delivery to the deployment site in a lumen. The delivery system includes a catheter 550, and a balloon 560 that is connected to the catheter 550. The stent 500 is placed over the balloon 560. The stent 500 includes a plurality of turns 522 that each include a plurality of struts 530. Adjacent struts 530 are connected within a turn 522 by crowns 532. Selected crowns 532 of adjacent turns may be connected with connections 540, which may be the same type of connections 40 discussed above.

To accommodate for the differences in stiffness of the stent 500 and the delivery system 510, a stiffening material 570 may be added to portions of the delivery system 510 to increase the stiffness of the delivery system 510 to minimize the stiffness gradient between the delivery system 510 and the stent 500. In the illustrated embodiment, more of the stiffening material 570 is added to a portion of the catheter 570 that is not located within the stent 500, after the stent 500 is mounted to the delivery system 510. The stiffening material 570 provides a transition for the delivery system 510, so that overall, the delivery system 510, together with the stent 500, has a constant stiffness as the stent 500 is tracked through the lumen and to the stent delivery site.

Thus, in addition to the design of the stent, discussed above, the design of the delivery system can also be used to influence the stiffness of the overall assembly (delivery system and stent) across the length of the stent, as well as the delivery system. By creating a section of the delivery system to be more stiff than the rest of the delivery system, and specifically designed to complement the stiffness of portions of the stent, a uniform stiffness of the stent and delivery system as a whole may be achieved. For example, the delivery system can be made more stiff in the central portion of a stent, if the central portion of the stent is less stiff than the end portions of the stent. Additionally, the delivery system can be made more stiff at the end portions of the stent to minimize the transition of the low stiffness delivery system to the stiffer stent. This may minimize the amount of flaring at the ends of the stent, as the 'kink' point is no longer at the end of the stent, but instead may be located away from the stent.

Thus, it is contemplated that various combinations of the above-described embodiments may be used to create a stent having the desired expansion and tracking properties and to generally minimize the change in stiffness across the length of the stent, as well as the delivery system.

The embodiments of the stents discussed above may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different metals, alloys or other materials. Embodiments of the stent may also be formed from hollow tubes, or tubes that have been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A stent comprising:
    a wave form comprising a plurality of substantially straight struts and a plurality of crowns, each crown connecting two adjacent struts within the wave form, the wave form being wrapped around a longitudinal axis to define a hollow cylinder having a plurality of turns, wherein each turn is defined by one complete revolution around the cylinder, the cylinder having a central portion terminating in first and second opposing end portions;
    wherein the central portion comprises a plurality of turns, each turn of the central portion having a substantially constant first pitch angle of greater than 0° and less than 90° relative to the longitudinal axis;
    wherein the first end portion comprises first and second turns, the first turn defining a stent end perpendicular to the longitudinal axis and having a second pitch angle of about 90° relative to the longitudinal axis, the second turn being disposed between the first turn and the central portion and having a third pitch angle relative to the longitudinal axis and sized between the first pitch angle and the second pitch angle;

wherein one or more struts located in the first and second turns have a length that is longer than the average length of all the struts of the stent and are each connected to an adjacent turn via a selected crown; and a plurality of connections between selected crowns from adjacent turns, wherein the connections are positioned along the stent substantially equally so that a density of the number of connections of the end portions is substantially equal to a density of the number of connections of the central portion, wherein the first pitch angle, the second pitch angle, and the third pitch angle are each defined by a line extending through adjacent struts in the respective turns substantially at a mid-point of each strut between adjacent bends.

2. The stent according to claim 1 wherein the second end portion is an inverted mirror image of the first end portion.

3. The stent according to claim 1, wherein the connections are fusions.

4. The stent according to claim 1, wherein the connections are welds.

5. A stent comprising:

a wave form comprising a plurality of substantially straight struts and a plurality of crowns, each crown connecting two adjacent struts within the wave form, the wave form being wrapped around a longitudinal axis to define a hollow cylinder having a plurality of turns, wherein each turn is defined by one complete revolution around the cylinder, the cylinder having a central portion terminating in first and second opposing end portions;

wherein the central portion comprises a plurality of turns, each turn of the central portion having a substantially constant first pitch angle of greater than 0° and less than 90° relative to the longitudinal axis;

wherein the first end portion comprises first and second turns, the first turn defining a stent end perpendicular to the longitudinal axis and having a second pitch angle of about 90° relative to the longitudinal axis, one or more struts located in the first turn having a length that is longer than the average length of all the struts of the stent, the second turn being disposed between the first turn and the central portion and having a third pitch angle relative to the longitudinal axis and sized between the first pitch angle and the second pitch angle; and a third turn being disposed between the second turn and the central portion and having a fourth pitch angle relative to the longitudinal axis and sized between first pitch angle and the third pitch angle;

a plurality of connections between selected crowns from adjacent turns, wherein the connections are positioned along the stent substantially equally so that a density of the number of connections of the end portions is substantially equal to a density of the number of connections of the central portion, wherein the first pitch angle, the second pitch angle, and the third pitch angle are each defined by a line extending through adjacent struts in the respective turns substantially at a mid-point of each strut between adjacent bends.

* * * * *